United States Patent [19]

Naef

[11] Patent Number: 5,037,966
[45] Date of Patent: Aug. 6, 1991

[54] AZO DYES CONTAINING A 3-AMINOBENZOTHIENOISOTHIAZOLE DIAZO COMPONENT

[75] Inventor: Rudolf Naef, Lupsingen, Switzerland

[73] Assignee: Ciba-Geigy Corporation, Ardsley, N.Y.

[21] Appl. No.: 486,487

[22] Filed: Feb. 28, 1990

[30] Foreign Application Priority Data

Mar. 1, 1989 [CH] Switzerland .................. 742/89

[51] Int. Cl.⁵ ............... C09B 29/039; C07D 513/04; D06P 1/18; D06P 1/39
[52] U.S. Cl. ............................. 534/740; 534/581; 534/752; 534/887; 548/212; 549/57
[58] Field of Search .................. 534/740, 752

[56] References Cited

FOREIGN PATENT DOCUMENTS 1533260 11/1978 United Kingdom .............. 534/752
1549185 7/1979 United Kingdom ............... 534/752

OTHER PUBLICATIONS

Gazz. Chim. Ital., 1978, 1081 (1-2), 57-62.

Barton et al., Comprehensive Organic Chemistry, vol. 4, pp. 976-993 and 1009-1020, Pergamon Press (1979).

Primary Examiner—Mary C. Lee
Assistant Examiner—Fiona T. Powers
Attorney, Agent, or Firm—George R. Dohmann; Edward McC. Roberts

[57] ABSTRACT

Dyes of the formula

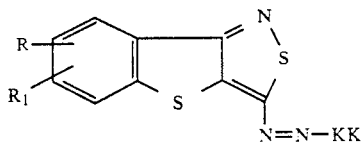

where R and $R_1$ are independently of the other hydrogen, halogen, nitro, alkyl or alkoxy and KK is the radical of a coupling component, which are particularly suitable for dyeing polyester fibers if no water-solubilizing group is present, and which are particularly suitable for dyeing and printing textile materials made of polyamide fibers when at least one sulfo group is present in the dye.

7 Claims, No Drawings

AZO DYES CONTAINING A 3-AMINOBENZOTHIENOISOTHIAZOLE DIAZO COMPONENT

The present invention relates to azo dyes derived from 3-aminobenzothienoisothiazole as diazo component, to the preparation of these azo dyes and to the use thereof as dyes for textile material.

The dyes according to the present invention conform to the formula

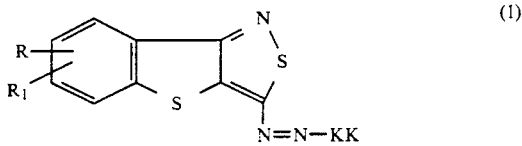

where R and $R_1$ are each independently of the other hydrogen, halogen, nitro, alkyl or alkoxy and KK is the radical of a coupling component.

Halogen is fluorine, bromine, iodine or in particular chlorine.

Alkyl according to the present invention is generally straight-chain, branched or cyclic alkyl. Examples are methyl, ethyl, propyl, i-propyl, butyl, i-butyl, tert-butyl, amyl, tert-amyl (1,1-dimethylpropyl), 1,1,3,3-tetramethylbutyl, hexyl, 1-methylpentyl, neopentyl, 1-, 2- or 3-methylhexyl, heptyl, n-octyl, tert-octyl, 2-ethylhexyl, n-nonyl, isononyl, decyl, dodecyl, cyclopentyl, cyclohexyl, methylcyclohexyl and the corresponding isomers. Alkyl preferably contains 1 to 6 carbon atoms, in particular 1 to 4 carbon atoms.

Alkyl may be substituted, for example by hydroxyl, alkoxy, cyano or phenyl. Examples of substituted alkyls are hydroxyethyl, methoxymethyl, ethoxyethyl, cyanoethyl, propoxypropyl and benzyl.

Suitable alkoxy preferably has 1-4 carbon atoms, such as methoxy, ethoxy, propoxy, isopropoxy, n-butoxy, isobutoxy or tert-butoxy.

R and $R_1$ are preferably each independently of the other hydrogen, chlorine, nitro, methyl or methoxy. Preferably, $R_1$ is hydrogen and R is hydrogen or chlorine.

Suitable coupling components KK are the customary azo dye coupling components known from the relevant literature.

Of the large number of possibilities, examples are coupling components of the benzene series, of the naphthalene series, of open-chain active methylene compounds (e.g. of acylacetarylamides) and of the heterocyclic series.

Examples of the coupling component KK radicals mentioned are radicals from the series of the acylacetarylamides, phenols, pyridones, quinolones, pyrazoles, indoles, diphenylamines, anilines, aminopyridines, pyrimidines, pyrimidones, naphthols, naphthylamines, aminothiazoles, thiophenes or hydroxypuridines.

Particularly noteworthy radicals KK are those from the series of the acetoacetanilides, phenols, anilines, diphenylamines, naphthylamines, naphthols, indoles, quinolines, pyridones, pyrazoles, quinolones and aminopyridines.

These coupling components may carry further substituents which are customary in dye chemistry for coupling components, for example hydroxyl, amino, alkylamino, dialkylamino, halogen, alkoxy, aryl, aryloxy, alkylcarbonylamino, arylcarbonylamino, alkylsulfonylamino or sulfo.

Owing to their particularly good dyeing properties, particular preference is given to those dyes of the formula (1) where KK is the radical of an aniline, naphthylamine or tetrahydroquinoline, which in each case may be substituted by $C_1$-$C_4$alkyl, $C_1$-$C_4$alkylcarbonylamino, phenyl, $C_1$-$C_4$alkylphenyl or sulfo.

Particularly preferred azo dyes according to the present invention are those of the formula (1) where R is hydrogen, chlorine, nitro, methyl or methoxy and KK is the radical of a coupling component from the series of the acetoacetanilides, phenols, anilines, diphenylamines, naphthylamines, naphthols, indoles, quinolines, pyridones, pyrazoles, quinolones and aminopyridines, which radicals are unsubstituted or substituted by hydroxyl, amino, alkylamino, dialkylamino, halogen, alkoxy, aryl, aryloxy, alkylcarbonylamino, arylcarbonylamino, alkylsulfonylamino or sulfo. Aryl here is for example naphthyl or in particular phenyl.

Of these, particular preference is given to those where is R is hydrogen or chlorine and KK is the radical of an aniline, naphthylamine or tetrahydroquinoline, which may in each case be substituted by $C_1$-$C_4$alkyl, $C_1$-$C_4$alkylcarbonylamino, phenyl, $C_1$-$C_4$alkylphenyl or sulfo.

The novel azo dyes of the formula (1) can be prepared by methods known per se. They are obtained for example by diazotizing a compound of the formula

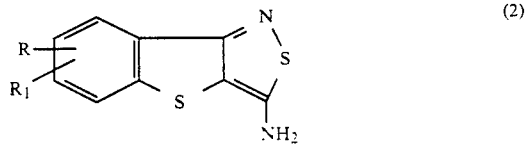

and coupling it onto a coupling component

where R, $R_1$ and KK are each as defined under the formula (1).

The compounds of the formula (2) are diazotized in a manner known per se, for example with sodium nitrite in an aqueous acid medium, for example in aqueous hydrochloric acid or sulfuric acid. However, the diazotization may also be carried out with other diazotizing agents, for example with nitrosylsulfuric acid. The diazotization can also be carried out with an additional acid present in the reaction medium, for example phosphoric acid, sulfuric acid, acetic acid, propionic acid, hydrochloric acid or mixtures thereof, for example mixtures of phosphoric acid and acetic acid. Advantageously, the diazotization is carried out at temperatures of $-10°$ to $30°$ C., for example from $-10°$ C. to room temperature.

The coupling of the diazotized compound of the formula (2) onto the coupling component H-KK is likewise carried out in a conventional manner, for example in an acid, aqueous or aqueous/organic medium, advantageously at temperatures of $-10°$ to $30°$ C., in particular below $10°$ C. The acids used are for example hydrochloric acid, acetic acid, sulfuric acid and phosphoric acid. Diazotization and coupling can be carried out for example in a one-pot process, i.e. within the same reaction medium.

The coupling components H-KK are known.

The compounds of the formula

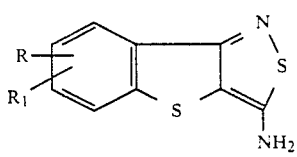
(2)

where R and R₁ are each hydrogen, halogen, nitro, alkyl or alkoxy, are novel and form a further part of the subject-matter of the present invention.

The compounds of the formula (2) are obtained for example by treating a compound of the formula

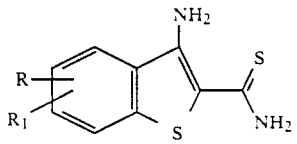
(4)

where R and R₁ are each hydrogen, halogen, nitro, alkyl or alkoxy, with an oxidizing agent in the presence of an organic base. The reaction is preferably carried out at a temperature between $-20°$ and $50°$ C., in particular between $-10°$ and $20°$ C., in an inert solvent for example dimethylformamide or dimethyl sulfoxide.

However, the reaction can also be carried out without an inert solvent, in which case the organic base is used in such an amount that it also serves as solvent.

The organic base used is for example pyridine, α-, β- or γ-picoline or a lutidine, e.g. 2,4- or 2,6-lutidine. Of these, pyridine is preferred.

The oxidizing agent used is in particular hydrogen peroxide, preferably as an aqueous solution.

The compounds of the formula

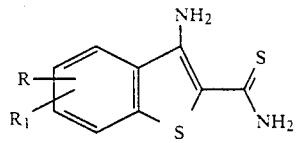
(4)

where R and R₁ are each hydrogen, halogen, nitro, alkyl or alkoxy, are novel and form a further part of the subject-matter of the present invention.

The compounds of the formula (4) are obtained for example by converting in compounds of the formula

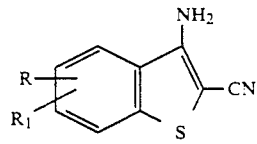
(5)

where R and R₁ are each hydrogen, halogen, nitro, alkyl or alkoxy, the nitrile group into a thioamide group in a conventional manner, for example by heating a compound of the formula (5) together with phosphorus pentasulfide to about $120°$ C., by heating an ethanolic solution of the compound of the formula (5) together with sulfur under reflux, by heating a compound of the formula (5) together with H₂S in liquid triethylamine in an autoclave to about $50°$ C., or preferably by passing H₂S at about $30°$ to $70°$ C. into a solution of a compound of the formula (5) in an inert solvent, e.g. dimethyl sulfoxide.

The compounds of the formula (5) are known or can be prepared in a known manner, for example as described in J. Org. Chem. 39, 3440 (1974).

If the compounds of the formula (1) according to the present invention do not contain any water-solubilizing groups, in particular no sulfo groups, they can be used as disperse dyes for dyeing and printing cellulosic or in particular synthetic hydrophobic fibre materials, in particular textile materials. Textile materials made of blend fabrics which contain such cellulosic or synthetic hydrophobic textile materials can likewise be dyed or printed with the aid of the compounds according to the present invention.

Suitable cellulosic textile materials are in particular cellulose acetate and cellulose triacetate.

Synthetic hydrophobic textile materials comprise in particular linear, aromatic polyesters, for example those of terephthalic acid and glycols, especially ethylene glycol, or condensation products of terephthalic acid and 1,4-bis(hydroxymethyl)cyclohexane, polycarbonates, for example those formed from α,α-dimethyl-4,4'-dihydroxydiphenylmethane and phosgene; and fibres based on polyvinyl chloride or polyamide.

The disperse dyes according to the present invention are applied to the textile materials by known dyeing methods. For example, polyester fibre materials are dyed by the exhaust method from an aqueous dispersion in the presence of customary anionic or nonionic dispersants and in the presence or absence of customary swelling agents (carriers) at temperatures between $80°$ and $140°$ C. Cellulose acetate is preferably dyed at between approximately $65°$ and $85°$ C. and cellulose triacetate at temperatures up to $115°$ C.

The novel disperse dyes do not go on any wool or cotton present in the dyebath at the same time to any great extent, if at all, and this property of a very good wool and cotton reserve also makes the novel disperse dyes highly suitable for dyeing polyester/wool and polyester/cellulose fibre blend fabrics.

The disperse dyes according to the present invention, however, are especially suitable for dyeing by thermosoling.

At the time of the application of the dyes according to the present invention the textile material mentioned can be in various states of processing, for example in the form of fibre, yarn, web, woven fabric or knitted fabric.

It is advantageous to convert the disperse dyes according to the present invention into a dye preparation before use. To this end, the dye is milled so that its particle size is on average between 0.01 and 10 microns. The milling can take place in the presence of dispersants. For example the dried dye is milled together with a dispersant or kneaded in paste form with a dispersant and then dried in vacuo or by spray-drying. The preparations thus obtained can be used for dyeing and printing on addition of water.

Printing will be carried out using the customary thickeners, for example modified or unmodified natural products, e.g. alginates, British gum, gum arabic, crystal gum, locust bean flour, tragacanth, carboxymethylcellulose, hydroxyethylcellulose, or starch, or synthetic products, e.g. polyacrylamides, polyacrylic acid or copolymers thereof or polyvinyl alcohols.

The disperse dyes according to the present invention are virtually insensitive to carrier and confer on the materials mentioned, in particular on polyester material, level blue to violet shades having very good end-use fastness properties, in particular good light fastness, fastness to dry heat setting and pleating, chlorine fastness and wet fastness such as water, perspiration and wash fastness; the dyeings are also notable for good pH stability and very good rub fastness. The dyeings are also very deep. It is particularly worth mentioning the good sublimation fastness and the good dry heat setting and pleating fastness of the dyeings obtained.

The dyes according to the present invention are also highly suitable for preparing mixed shades together with other dyes. It is of course also possible to use mixtures between the dyes according to the present invention.

If the monoazo dyes of the formula (1) contain a sulfo group, it is present either in the form of the free sulfonic acid or preferably as a salt thereof. Suitable salts are for example the alkali metal, alkaline earth metal or ammonium salts or the salts of an organic amine. Examples are the sodium, lithium, potassium and ammonium salts and the salt of triethanolamine.

The sulfo-containing azo dyes of the formula (1) can be isolated and processed into usable, dry dyeing preparations. Isolation preferably takes place at very low temperatures by salting out and filtering. After filtration, the dyes are dried with or without the addition of extenders and/or buffers, for example with the addition of a mixture of equal parts of monosodium phosphate and disodium phosphate; preferably, the drying is carried out at moderate temperatures and under reduced pressure. By spray-drying the entire synthesis mixture it is possible in certain cases to prepare the dry preparations according to the present invention directly, i.e. without intermediary isolation of the dyes.

The sulfo-containing azo dyes of the formula (1) are suitable for dyeing and printing a wide variety of materials but in particular silk, wool and nylon fibres. They are suitable not only for the exhaust method but also for dyeing by the pad dyeing method, whereby the material is impregnated with aqueous and possibly also salt-containing dye solutions.

They are also suitable for printing nitrogen-containing fibres, for example wool, nylons or silk- or wool-containing blend fabrics.

It is advisable to subject the dyeings and prints to a thorough rinse with cold and hot water in the presence or absence of a dispersant which promotes the diffusion of the unfixed portions.

The sulfo-containing azo dyes of the formula (1) produce dyeings of good wet and light fastness properties. It is particularly worth mentioning that the dyes show good solubility, especially electrolyte solubility, combined with good exhaustion properties and high degrees of dye fixation and that the unfixed portions are easily removable. Besides being readily water-soluble, the sulfo-containing azo dyes of the formula (1) give very stable solutions in padding liquors over a wide pH range and very stable print pastes.

In the examples which follow, parts and % are by weight. The temperatures are degrees Celcius.

EXAMPLE 1

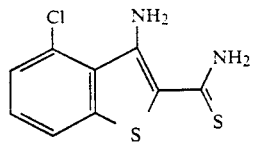

4.2 g (20 mmol) of 3-amino-4-chloro-2-cyanobenzo[b]-thiophene are dissolved in 55 ml of dimethyl sulfoxide, and hydrogen sulfide gas is introduced at 50° C. over 24 hours, during which the product gradually precipitates. The precipitation is completed by adding water. 4.3 g are obtained of a crude product which is filtered off. Recrystallization from dimethylformamide/water leaves a yellow powder of melting point 190° C.

EXAMPLE 2

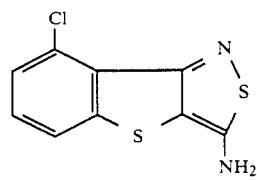

36 g (148 mmol) of 3-amino-2-thioamido-4-chlorobenzo[b]thiophene are dissolved in a mixture of 150 ml of dimethylformamide and 50 ml of pyridine, and 24.5 ml (280 mmol) of 40% aqueous hydrogen peroxide solution are slowly added dropwise at 0° C. The mixture is stirred at room temperature for 24 hours and filtered, and water is added to the mother liquor to precipitate 27.9 g of a crude product which on recrystallization from ethanol/water leaves a yellowish powder of melting point >250° C.

EXAMPLE 3

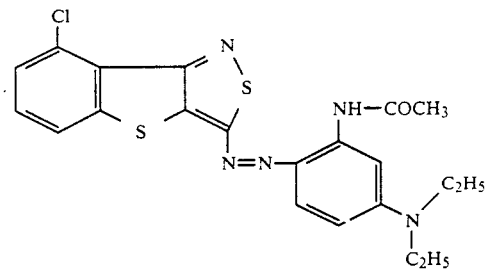

1.45 g (6 mmol) of 3-amino-8-chlorobenzo[b]thieno[4,5-c]isothiazole are suspended in a mixture of 30 ml of acetic acid and 10 ml of propionic acid, 3.5 ml of concentrated sulfuric acid are added, the mixture is cooled down to 0° C., and 0.4 g of sodium nitrite in 10 ml of water is added for a diazotization. The yellow diazonium salt solution is then added dropwise to a solution of 1.5 g (6 mmol) of 3-N,N-diethylaminoacetanilide in a mixture of 20 ml of acetic acid and 25 ml of ethanol, immediately forming a reddish violet precipitate which is filtered off and washed with water. Recrystallization from dimethylformamide/water leaves 1 g of a violet powder of melting point >250° C., which dyes polyester fibres in brilliant violet shades.

EXAMPLE 4-7

The method described in Example 3 is repeated to obtain the azo dyes listed in the table below by diazotizing the azo component obtained as described in Example 2 and coupling it with the corresponding coupling components. Column 3 of the table indicates the shades of dyeings on polyester textile material.

ml of ethanol and 4 g of sodium acetate while the temperature is maintained below 5° C. by the addition of ice and the pH is maintained at about 3.5 by the continuous addition of 2N sodium hydroxide solution. The oily dark blue precipitate is filtered off with suction and recrystallized from dimethylformamide/water.

The dye conforms to the formula

| Example | Dye | Shade on polyester |
|---|---|---|
| 4 | *(structure)* | bluish red |
| 5 | *(structure)* | bluish red |
| 6 | *(structure)* | dull violet |
| 7 | *(structure)* | claret |

EXAMPLE 8

2.4 g of 3-amino-8-chlorobenzo[b]thieno[4,5-c]isothiazole are suspended in a mixture of 40 ml of glacial acetic acid and 10 ml of propionic acid, the suspension is cooled down to 0° C., and 5 ml of concentrated sulfuric acid are added. 0.7 g of sodium nitrite dissolved in 10 ml of water are then added dropwise with thorough cooling, and the suspension gradually turns into a pink solution. The solution obtained is added dropwise to a solution of 3.2 g of 1-(4-toluidino)naphthalene-8-sulfonic acid in a mixture of 30 ml of glacial acetic acid, 40

EXAMPLES 9-10

The method described in Example 8 is also used to obtain the azo dyes listed in the table below by diazotizing the diazo component obtained as described in Example 2 and coupling it with the corresponding coupling components. Column 3 of the table indicates the shades of dyeings on polyamide textile material.

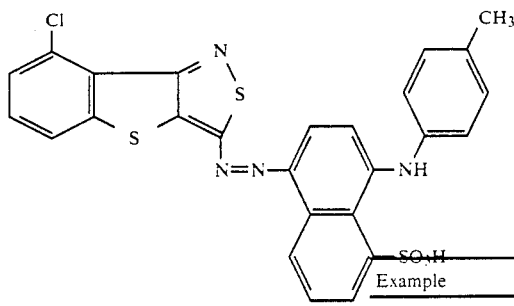

and dyes polyamide textile material in brilliant blue shades.

| Example | Dye | Shade on polyamid |
|---|---|---|
| 9 | (structure shown) | ruby |
| 10 | (structure shown) | reddish navy |

EXAMPLES 11-58

The method described in Example 3 is followed to obtain analogous azo dyes by diazotizing the diazo components listed in column 2 of the table below and coupling them with the coupling components listed in column 3. Column 4 indicates the shades of dyeings on polyester textile material.

| Example | Diazo component | Coupling component | Shade on PES |
|---|---|---|---|
| 11 | (structure shown) | (structure shown) | violet |
| 12 | (structure shown) | (structure shown) | reddish violet |
| 13 | (structure shown) | (structure shown) | violet |

-continued
| Example | Diazo component | Coupling component | Shade on PES |
|---|---|---|---|
| 14 | 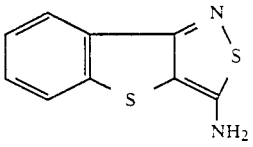 | 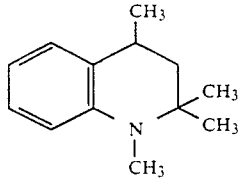 | reddish violet |
| 15 | 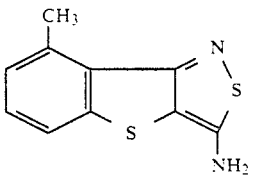 | 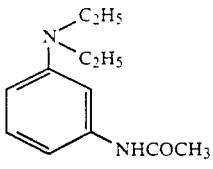 | violet |
| 16 | 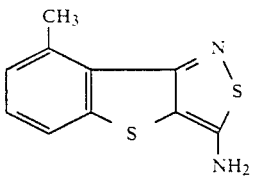 | 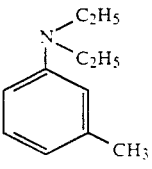 | reddish violet |
| 17 | 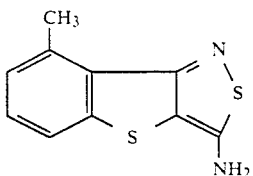 | 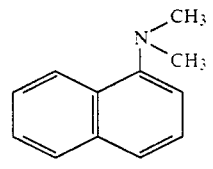 | violet |
| 18 | 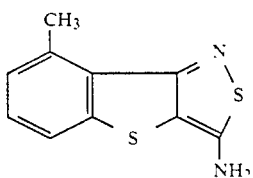 | 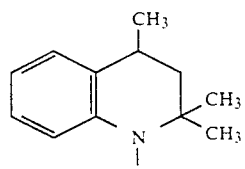 | reddish violet |
| 19 | 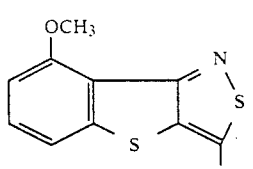 | 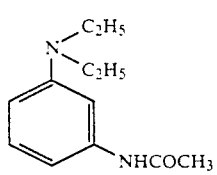 | reddish violet |
| 20 | 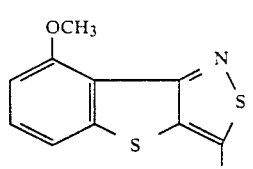 | 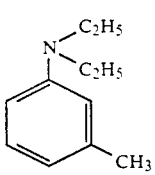 | violet-tinged red |
| 21 | 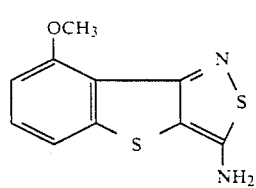 | 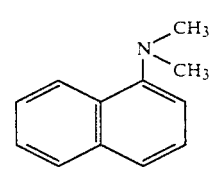 | violet |

-continued

| Example | Diazo component | Coupling component | Shade on PES |
|---|---|---|---|
| 22 | 3-amino-4-(2-methoxyphenyl)isothiazolo-benzothiophene | 1,2,2,4-tetramethyl-1,2,3,4-tetrahydroquinoline | violet |
| 23 | 3-amino-4-(2-nitrophenyl)isothiazolo-benzothiophene | 3-(N,N-diethylamino)acetanilide | violet |
| 24 | 3-amino-4-(2-nitrophenyl)isothiazolo-benzothiophene | N,N-diethyl-3-methylaniline | violet |
| 25 | 3-amino-4-(2-nitrophenyl)isothiazolo-benzothiophene | N,N-dimethyl-1-naphthylamine | bluish violet |
| 26 | 3-amino-4-(2-nitrophenyl)isothiazolo-benzothiophene | 1,2,2,4-tetramethyl-1,2,3,4-tetrahydroquinoline | bluish violet |
| 27 | 3-amino-4-(2,4-dinitrophenyl)isothiazolo-benzothiophene | 3-(N,N-diethylamino)acetanilide | blue-violet |
| 28 | 3-amino-4-(2,4-dinitrophenyl)isothiazolo-benzothiophene | N,N-diethyl-3-methylaniline | violet |
| 29 | 3-amino-4-(2,4-dinitrophenyl)isothiazolo-benzothiophene | N,N-dimethyl-1-naphthylamine | bluish violet |

-continued

| Example | Diazo component | Coupling component | Shade on PES |
|---|---|---|---|
| 30 | 4,6-dinitro-benzothieno-isothiazole-3-amine | 1,2,2,4-tetramethyl-1,2,3,4-tetrahydroquinoline | violet |
| 31 | 7-chloro-benzothieno-isothiazole-3-amine | 3-cyano-2,6-dihydroxy-4-methylpyridine | yellow |
| 32 | 7-chloro-benzothieno-isothiazole-3-amine | 1-methyl-2-phenylindole | bordeaux |
| 33 | 7-chloro-benzothieno-isothiazole-3-amine | phenol | orange |
| 34 | 7-chloro-benzothieno-isothiazole-3-amine | 3-methyl-1-phenyl-5-hydroxypyrazole | yellowish brown |
| 35 | 7-chloro-benzothieno-isothiazole-3-amine | ethyl 3-(phenylcarbamoyl)propanoate (CH$_2$–COOC$_2$H$_5$, CONH–Ph) | yellow |
| 36 | 7-chloro-benzothieno-isothiazole-3-amine | 2,4-dihydroxyquinoline | reddish yellow |
| 37 | 7-chloro-benzothieno-isothiazole-3-amine | N-(2-hydroxyethyl)-N-(2-cyanoethyl)aniline | bordeaux |

-continued

| Example | Diazo component | Coupling component | Shade on PES |
|---|---|---|---|
| 38 | 4-Cl-benzo[b]thieno-isothiazole-3-amine | N(C₂H₄OH)(C₂H₄OC(O)CH₃)-phenyl | reddish violet |
| 39 | 4-Cl-benzo[b]thieno-isothiazole-3-amine | N(C₂H₅)(C₂H₄Cl)-phenyl | bordeaux |
| 40 | 4-Cl-benzo[b]thieno-isothiazole-3-amine | N(C₂H₄OCH₃)(C₂H₄OH)-phenyl | reddish violet |
| 41 | 4-Cl-benzo[b]thieno-isothiazole-3-amine | N(C₂H₅)(C₂H₄OCOCH₃)-phenyl | reddish violet |
| 42 | 4-Cl-benzo[b]thieno-isothiazole-3-amine | N(C₂H₄OH)(C₂H₄CN)-phenyl | bordeaux |
| 43 | 4-Cl-benzo[b]thieno-isothiazole-3-amine | N(C₂H₄OCH₃)(C₂H₄OCOCH₃)-phenyl | bordeaux |
| 44 | 4-Cl-benzo[b]thieno-isothiazole-3-amine | N(CH₃)(CH₃)-phenyl | bordeaux |
| 45 | 4-Cl-benzo[b]thieno-isothiazole-3-amine | N(C₂H₄OCH₃)(C₂H₄CO₂CH₃)-phenyl | reddish violet |

| Example | Diazo component | Coupling component | Shade on PES |
|---|---|---|---|
| 46 | 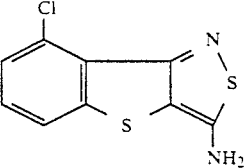 | 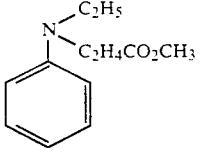 | reddish violet |
| 47 | 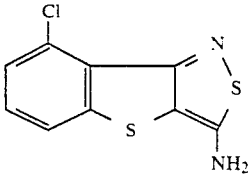 | 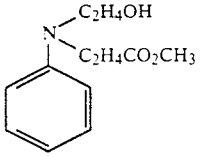 | reddish violet |
| 48 | 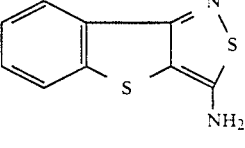 | 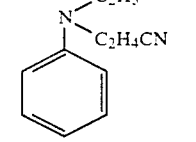 | bordeaux |
| 49 | 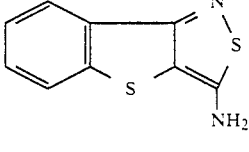 | 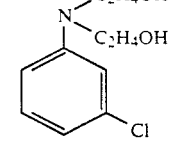 | bordeaux |
| 50 | 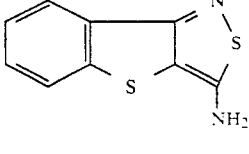 | 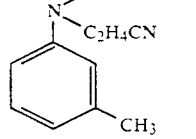 | bordeaux |
| 51 | 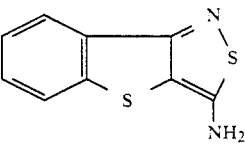 | 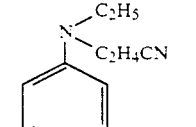 | reddish violet |
| 52 | 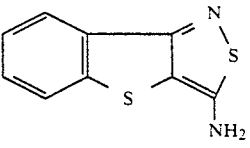 | 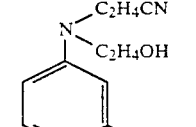 | reddish violet |
| 53 | 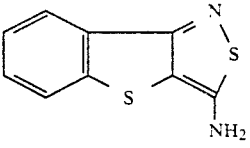 | 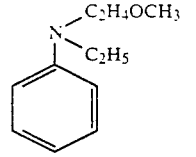 | bordeaux |
| 54 | 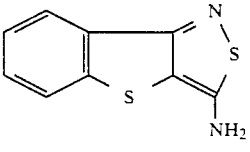 | 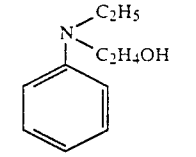 | reddish violet |

-continued

| Example | Diazo component | Coupling component | Shade on PES |
|---|---|---|---|
| 55 | benzothiophene-isothiazole-NH₂ | N(CH₃)(C₂H₄CO₂CH₃), 3-Cl-phenyl | brownish red |
| 56 | benzothiophene-isothiazole-NH₂ | N(C₂H₄OH)(C₂H₄OH), 3-CH₃-phenyl | reddish violet |
| 57 | benzothiophene-isothiazole-NH₂ | N(C₂H₅)(C₃H₆NHCOCH₃), 3-CH₃-phenyl | violet |
| 58 | benzothiophene-isothiazole-NH₂ | N(C₂H₅)(C₂H₄OH), 3-CH₃-phenyl | reddish violet |

EXAMPLES 59–90

The method described in Example 8 is followed to obtain the analogous azo dyes by diazotizing the diazo components listed in column 2 of the table below and coupling them with the coupling components listed in column 3. Column 4 indicates the shades of dyeings on polyamide textile material.

| Example | Diazo component | Coupling component | Shade on polyamide |
|---|---|---|---|
| 59 | benzothiophene-isothiazole-NH₂ | 8-NaO₃S-naphthyl-NH-(4-CH₃-phenyl) | greenish blue |
| 60 | benzothiophene-isothiazole-NH₂ | 6-NaO₃S-2-NH₂-naphthalene | red |
| 61 | benzothiophene-isothiazole-NH₂ | 3-CH₃-5-NH₂-1-(4-SO₃Na-phenyl)pyrazole | orange-yellow |

65

-continued

| Example | Diazo component | Coupling component | Shade on polyamide |
|---|---|---|---|
| 62 | benzothieno-isothiazole-NH₂ | 4-[N(CH₃)(CH₂CH₂SO₃Na)]aniline | violet |
| 63 | benzothieno-isothiazole-NH₂ | 4-[N(phenyl)(CH₂CH₂SO₃Na)]aniline | reddish violet |
| 64 | benzothieno-isothiazole-NH₂ | 3-methoxy-N-benzyl-N-(CH₂CH₂SO₃Na)aniline | reddish violet |
| 65 | benzothieno-isothiazole-NH₂ | N-ethyl-N-(3-sulfobenzyl)aniline, Na salt | violet |
| 66 | benzothieno-isothiazole-NH₂ | N-ethyl-N-(3-sulfobenzyl)-3-methoxyaniline, Na salt | reddish violet |
| 67 | benzothieno-isothiazole-NH₂ | 5-sulfo-1,2-dimethylindole, Na salt | bordeaux |
| 68 | benzothieno-isothiazole-NH₂ | 5-sulfo-2-phenylindole, Na salt | red |
| 69 | benzothieno-isothiazole-NH₂ | 4-methyl-2-[N(CH(CH₃)CH₂O-)(CH₂CH₂SO₃Na)]aniline-type coupler | blue |
| 70 | 4-methoxy-benzothieno-isothiazole-NH₂ | 8-sulfo-1-(4-methylphenylamino)naphthalene, Na salt | greenish blue |

-continued

| Example | Diazo component | Coupling component | Shade on polyamide |
|---------|-----------------|--------------------|--------------------|
| 71 | [benzothiophene-isothiazole with OCH₃ and NH₂] | 6-amino-2-naphthalenesulfonate (NaO₃S, NH₂) | red |
| 72 | [benzothiophene-isothiazole with OCH₃ and NH₂] | 3-methyl-5-amino-1-(4-sulfophenyl)pyrazole (SO₃Na) | orange-yellow |
| 73 | [benzothiophene-isothiazole with OCH₃ and NH₂] | N-methyl-N-(2-sulfoethyl)aniline | violet |
| 74 | [benzothiophene-isothiazole with OCH₃ and NH₂] | N,N-diphenyl-2-sulfoethylamine | reddish violet |
| 75 | [benzothiophene-isothiazole with OCH₃ and NH₂] | N-benzyl-N-(2-sulfoethyl)-3-methoxyaniline | reddish violet |
| 76 | [benzothiophene-isothiazole with OCH₃ and NH₂] | N-ethyl-N-(3-sulfobenzyl)aniline | violet |
| 77 | [benzothiophene-isothiazole with OCH₃ and NH₂] | N-ethyl-N-(3-sulfobenzyl)-3-methoxyaniline | reddish violet |
| 78 | [benzothiophene-isothiazole with OCH₃ and NH₂] | 1,2-dimethyl-5-sulfoindole (NaO₃S) | bordeaux |

-continued
| Example | Diazo component | Coupling component | Shade on polyamide |
|---|---|---|---|
| 79 | 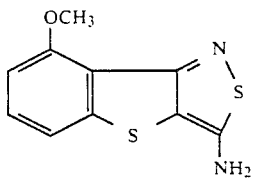 | 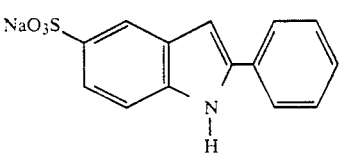 | red |
| 80 | 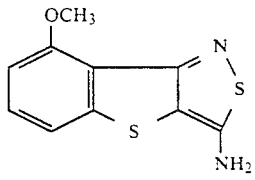 | 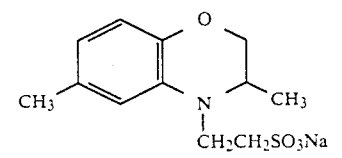 | blue |
| 81 | 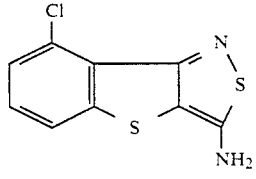 | 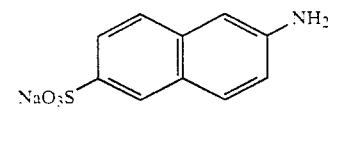 | red |
| 82 | 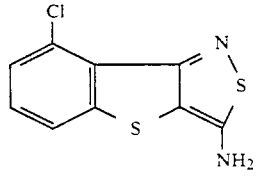 | 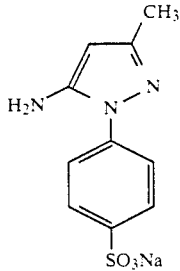 | orange-yellow |
| 83 | 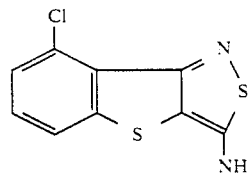 | 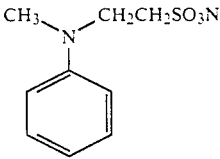 | violet |
| 84 | 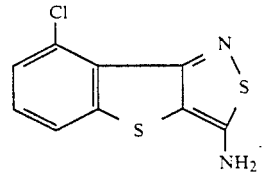 | 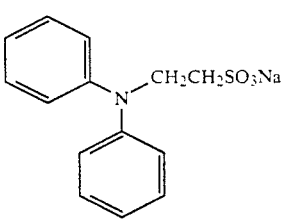 | reddish violet |
| 85 | 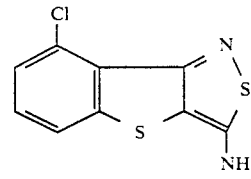 | 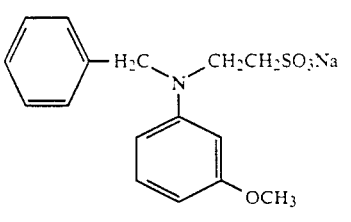 | reddish violet |
| 86 | 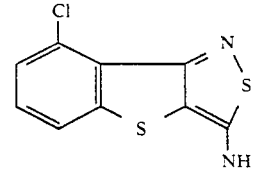 | 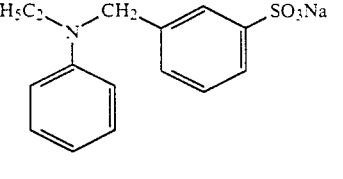 | violet |

-continued

| Example | Diazo component | Coupling component | Shade on polyamide |
|---|---|---|---|
| 87 | 4-Cl benzo[thieno]isothiazole-3-amine | H₅C₂-N(CH₂-C₆H₄-SO₃Na)-C₆H₄-OCH₃ | reddish violet |
| 88 | 4-Cl benzo[thieno]isothiazole-3-amine | 5-NaO₃S-2-methyl-1-methylindole | bordeaux |
| 89 | 4-Cl benzo[thieno]isothiazole-3-amine | 5-NaO₃S-2-phenyl-1H-indole | red |
| 90 | 4-Cl benzo[thieno]isothiazole-3-amine | 4-methyl-N-(1-methyl-2-(sodiosulfoethyl))amino-phenoxypropane derivative | blue |

EXAMPLE 91

1 part of the dry, extender-free dye of Example 3 is mixed in a sand mill together with 2 parts of dinaphthylmethanedisulfonate (Na salt), 34 parts of quartz sand and 17 parts of water, and the mixture is milled until the particle size is about 2 μm or less. The suspension formed is separated from the sand and spray-dried, giving a pulverulent dyeing preparation.

EXAMPLE 92

Polyethylene terephthalate fabric is impregnated on a pad-mangle at 40° C. with a liquor of the following composition:
20 parts of dye preparation obtained as described in Example 91, finely dispersed in
10 parts of sodium alginate,
20 parts of octylphenol polyglycol ether and
930 parts of water.

The fabric is squeezed off to about 60%, dried at 100° C. and then thermofixed at 210° C. for 60 seconds. The dyed material is rinsed with water, soaped off or reduction cleared and dried. The result obtained is a light-fast violet dyeing which is notable in particular for good sublimation fastness.

EXAMPLE 93

2 parts of the dye preparation obtained as described in Example 91 are dispersed in 4,000 parts of water containing 12 parts of the sodium salt of o-phenylphenol, 2 parts of ammonium sulfate and 2 parts of the sodium salt of dinaphthylmethanedisulfonic acid. This liquor is then used to dye 100 parts of polyethylene terephthalate yarn at 95°–98° C. for 90 minutes.

The dyeing is subsequently rinsed and aftertreated with aqueous sodium hydroxide solution and a dispersant. The result obtained in this way is a light- and sublimation-fast violet dyeing.

EXAMPLE 94

1 part of the dye obtained as described in Example 4 is wet-milled with 2 parts of a 50% aqueous solution of the sodium salt of dinaphthylmethanedisulfonic acid and dried.

This dye preparation is stirred up with 40 parts of a 10% aqueous solution of the sodium salt of N-benzyl-heptadecylbenzimidazoledisulfonic acid, and 4 parts of a 40% acetic acid solution are added. Water is then added to prepare a dyebath of 4,000 parts.

This bath is entered at 50° C. with 100 parts of polyester fibre material, the temperature is raised to 120°–130° C. in the course of half an hour, and dyeing is carried out at that temperature in a closed vessel for an hour. This is followed by a thorough rinse. The result obtained is a bluish red dyeing having good fastness properties, in particular good sublimation and thermomigration fastness properties.

EXAMPLE 95

10 parts of Helanca (polyamide) tricot are dyed in 500 parts of aqueous liquor containing 2 g/l of ammonium acetate and adjusted to pH 5 with acetic acid. The liquor contains 0.7% of the dye of Example 8 on weight of fibre. The dyeing time at 98° C. is 30 to 90 minutes. The dyed piece of Helanca is subsequently removed and washed and dried in the usual manner.

The result obtained on the Helanca is a brilliant blue dyeing which has good all round fastness properties.

EXAMPLE 96

10 parts of Helanca (polyamide) tricot are dyed in 500 parts of aqueous liquor which contains 1 g/l of monosodium phosphate and is adjusted to pH 6 with disodium phosphate. The liquor contains 1% of the dye of Example 8 on weight of fibre. The dyeing time at 98° C. is 30 to 90 minutes. The dyed Helanca is then removed and washed and dried in the usual manner.

The result obtained on the Helanca is a blue dyeing which has a pure shade and good all round fastness properties.

EXAMPLE 97

10 parts of wool piece goods are dyed in 500 parts of an aqueous liquor containing, on weight of fibre, 0.45% of dye of Example 9,5% of calcined Glauber's salt and 4% of 96% sulfuric acid. The dyeing time at 98° C. is 30-60 minutes. The wool, which is washed and dried in the usual manner, is dyed to a ruby shade having very good all round fastness properties.

What is claimed is:

1. A dye of the formula

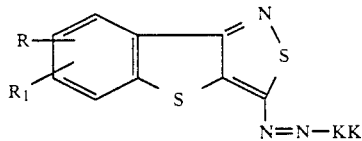

where R and $R_1$ are independently of the other hydrogen, halogen, nitro, $C_1$–$C_4$-alkoxy or $C_1$–$C_{12}$-alkyl which is unsubstituted or substituted by hydroxy, $C_1$–$C_4$-alkoxy, cyano or phenyl and KK is the radical of a coupling component.

2. A dye according to claim 1, wherein R is hydrogen, chlorine, nitro, methyl or methoxy and $R_1$ is hydrogen.

3. A dye according to either of claims 1 and 2, wherein KK is the radical of a coupling component selected from the group consisting of acylacetarylamides, phenols, pyridones, quinolones, pyrazoles, indoles, diphenylamines, anilines, aminopyridines, pyrimidines, pyrimidones, naphthols, naphthylamines, aminothiazoles, thiophenes, hydroxypyridines and quinolines.

4. A dye according to claim 3, wherein KK is the radical of a coupling component selected from the group consisting of the acetoacetanilides, phenols, anilines, diphenylamines, naphthylamines, naphthols, indoles, quinolines, pyridones, pyrazoles, quinolones and aminopyridines, which coupling component is unsubstituted or substituted by hydroxyl, amino, $C_1$–$C_6$-alkylamino, di-$C_1$–$C_6$-alkylamino, halogen, $C_1$–$C_4$-alkoxy, phenyl, phenoxy, $C_1$–$C_4$-alkylcarbonylamino, phenylcarbonylamino, $C_1$–$C_4$-alkylsulfonylamino $C_1$–$C_4$-alkyl, $C_1$–$C_4$-alkylphenyl or sulfo.

5. A dye according to claim 4, wherein KK is the radical of an aniline, naphthylamine or tetrahydroquinoline, which are unsubstituted or substituted by $C_1$–$C_4$alkyl, $C_1$–$C_4$alkylcarbonylamino, phenyl, $C_1$–$C_4$alkylphenyl or sulfo.

6. A dye according to claim 1, wherein $R_1$ is hydrogen, R is hydrogen, chlorine nitro, methyl or methoxy and KK is the radical of a coupling component selected from the group consisting of acetoacetanilides, phenols, anilines, diphenylamines, naphthylamines, naphthols, indoles, quinolines, pyridones, pyrazoles, quinolones and aminopyridines, which coupling component is unsubstituted or substituted by hydroxyl, amino, $C_1$–$C_6$-alkylamino, di-$C_1$–$C_6$-alkylamino, halogen, $C_1$–$C_4$-alkoxy, phenyl, phenoxy, $C_1$–$C_4$-alkylcarbonylamino, phenylcarbonylamino, $C_1$–$C_4$-alkylsulfonylamino or sulfo.

7. A dye according to claim 1, wherein R and $R_1$ are each hydrogen or chlorine and KK is the radical of an aniline, naphthylamine or tetrahydroquinoline, which are unsubstituted or substituted by $C_1$–$C_4$alkyl, $C_1$–$C_4$alkylcarbonylamino, phenyl, $C_1$–$C_4$alkylphenyl or sulfo.

* * * * *